(12) United States Patent
Przybylinski et al.

(10) Patent No.: US 6,596,911 B2
(45) Date of Patent: Jul. 22, 2003

(54) COMPOSITION AND METHOD FOR INHIBITION OF FORMATION OF GAS HYDRATES

(75) Inventors: John L. Przybylinski, Missouri City, TX (US); Gordon T. Rivers, Houston, TX (US)

(73) Assignee: Baker Hughes Incorporation, Houston, TX (US)

( * ) Notice: Subject to any disclaimer, the term of this patent is extended or adjusted under 35 U.S.C. 154(b) by 0 days.

(21) Appl. No.: 09/789,029

(22) Filed: Feb. 20, 2001

(65) Prior Publication Data

US 2002/0038063 A1 Mar. 28, 2002

Related U.S. Application Data

(60) Provisional application No. 60/184,016, filed on Feb. 22, 2000.

(51) Int. Cl.$^7$ .................................................. C07C 7/20
(52) U.S. Cl. .............................. 585/15; 585/2; 585/4; 585/950; 95/153
(58) Field of Search .................... 585/2, 4, 15, 950; 95/153

(56) References Cited

U.S. PATENT DOCUMENTS

| | | | | |
|---|---|---|---|---|
| 5,460,728 A | | 10/1995 | Klomp et al. ............... 210/698 |
| 5,648,575 A | | 7/1997 | Klomp et al. ............... 585/15 |
| 5,879,561 A | * | 3/1999 | Klomp et al. ............... 210/698 |
| 5,958,844 A | | 9/1999 | Sinquin et al. ............... 507/90 |
| 6,063,972 A | * | 5/2000 | Duncum et al. ............... 137/13 |
| 6,102,986 A | * | 8/2000 | Klug ........................... 585/15 |
| 6,152,993 A | * | 11/2000 | Klomp ........................ 585/15 |
| 6,180,699 B1 | * | 1/2001 | Bakeev et al. ................ 137/13 |
| 6,214,091 B1 | * | 4/2001 | Klomp ........................ 585/15 |
| 6,369,004 B1 | * | 4/2002 | Klug et al. .................... 137/13 |

FOREIGN PATENT DOCUMENTS

| | | |
|---|---|---|
| WO | WO-93/25798 A1 * | 12/1993 |
| WO | WO 95/17579 | 6/1995 |
| WO | WO 96/04462 A1 | 2/1996 |
| WO | WO 96/29502 | 9/1996 |
| WO | WO 96/34177 | 10/1996 |
| WO | WO-98/23843 A1 * | 6/1998 |

* cited by examiner

*Primary Examiner*—Walter D. Griffin
(74) *Attorney, Agent, or Firm*—Madan, Mossman & Sriram, P.C.

(57) ABSTRACT

A method and a composition used therein are disclosed for inhibiting formation of hydrocarbon hydrates. The composition comprises an onium compound, an amine salt and, optionally, a solvent. The method and composition are particularly useful for oil and gas production

15 Claims, No Drawings

COMPOSITION AND METHOD FOR INHIBITION OF FORMATION OF GAS HYDRATES

This patent application claims priority from U.S. Provisional Patent Application No. 60/184,016 filed Feb. 22, 2000.

BACKGROUND OF THE INVENTION

1. Field of the Invention

This invention relates to a method and a composition thereof for inhibiting the formation of hydrocarbon hydrates. This invention particularly related to a method and a composition thereof for inhibiting the formation of hydrocarbon hydrates during the production of oil and gas.

2. Background of the Invention

A number of hydrocarbons, especially lower-boiling light hydrocarbons, in formation fluids or natural gas are known to form hydrates with the water present in the system under a variety of conditions—particularly at a combination of lower temperature and higher pressure. The hydrates usually exist in solid forms that are essentially insoluble in the fluid itself. As a result, any solids in a formation fluid or natural gas liquid are at least a nuisance for production, handling and transport of the same. If the hydrate solids (or crystals) are concentrated enough, large enough themselves, and/or forming large agglomerates, it is not uncommon for them to cause plugging and/or blockage of pipelines or transfer lines or other conduits, valves and/or safety devices and/or other equipment, resulting in shutdown, loss of production and risk of explosion or unintended release of hydrocarbons into the environment either on-land or off-shore. Accordingly, hydrocarbon hydrates have been of substantial interest as well as concern to many industries, particularly the petroleum and natural gas industries.

Typically, the hydrocarbon hydrates are considered to be clathrates, also referred to as inclusion compounds. Clathrates are formed between a host molecule and a guest molecule. A hydrocarbon hydrate generally has crystals formed by having water host molecules surrounding the hydrocarbon guest molecules. The smaller or lower-boiling hydrocarbon molecules, particularly $C_1$ (methane) to $C_4$ hydrocarbons and their mixtures, tend to have more serious problems because it is believed that their hydrate or clathrate crystals are easier to form. For instance, it is believed that ethane would form hydrates at as high as 4° C. at a pressure of about 1 MPa. If the pressure is about 3 MPa, ethane hydrates can form at as high a temperature as 14° C. Even certain non-hydrocarbons such as carbon dioxide and hydrogen sulfide also are known to form hydrates under certain conditions.

There are two broad approaches to overcome or control the hydrocarbon hydrate problems, namely the thermodynamic approach and the kinetic approach. For the thermodynamic approach, there are a number of reported or attempted methods, including water removal, increasing temperature, decreasing pressure, addition of "antifreeze" to the fluid and/or a combination of these. The kinetic approach generally attempts (a) to prevent the smaller hydrocarbon hydrate crystals from agglomerating into larger ones; (b) to inhibit the hydrocarbon hydrates from being formed in the first place; (c) to slow down crystal formation or growth under a particular set of conditions; and/or a certain combination.

Efforts to control hydrates have included use of different materials as inhibitors. For instance, U.S. Pat. Nos. 5,460, 728 and 5,648,575 disclose a number of onium compounds with at least four carbon substituents which are used to inhibit the plugging of conduits by gas hydrates. U.S. Pat. No. 5,880,319 discloses additives such as polymers with lactam rings to control clathrate hydrates in fluid systems.

SUMMARY OF THE INVENTION

In one aspect, the present invention is a method for inhibiting formation of hydrocarbon hydrates, the method comprising: providing a mixture comprising water and a hydrocarbon; and contacting a composition comprising a first amount of an onium compound and a second amount of an amine salt with the mixture under conditions effective to form the hydrocarbon hydrates in the absence of the composition, wherein the first amount of the onium compound and the second amount of the amine salt in the composition are effective in inhibiting the formation of the hydrocarbon hydrates under the conditions.

In another aspect, the present invention is a method for inhibiting formation of hydrocarbon hydrates, the method comprising: providing a mixture comprising water and a hydrocarbon; and contacting a composition comprising a first amount of an onium compound, a second amount of an amine salt and a third amount of a solvent with the mixture under conditions effective to form the hydrocarbon hydrates in the absence of the composition, wherein the first amount of the onium compound is in the range of from about 5 volume % to about 75 volume %; the second amount of the amine salt in the range of from about 10 volume % to about 95 volume %, and the third amount of solvent is the range of from 0 volume % to about 85 volume %, all based on total volume of the composition.

In yet another aspect, the present invention is a composition for inhibiting formation of hydrocarbon hydrates from a mixture comprising water and a hydrocarbon, the composition comprising a first amount of an onium compound and a second amount of an amine salt, wherein the amine salt comprises a cation moiety and an anion moiety, the cation moiety is derived from an amine selected from group consisting of amines having the general formula:

(a) $R^a R^b R^c N$, and (b)

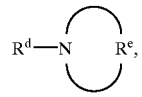

and mixtures thereof, wherein $R^a$, $R^b$, $R^c$, and $R^d$ are independently selected from the group consisting of H, $C_1$–$C_3$ alkyls and OH substituted $C_1$–$C_3$ alkyls; $R_e$ is selected from the group consisting of —$(CH_2)_m$— and —$(CH_2)_n$—Z—$(CH_2)_p$—, wherein Z is selected from O, S and $CHR^f$ and m is selected from 3 to 7; n, from 1 to 3; and p, from 1 to 4; $R^f$ is selected from H, $C_1$–$C_3$ alkyls and OH substituted $C_1$–$C_3$ alkyls.

In still another aspect, the present invention is a hydrocarbon composition inhibited against hydrocarbon hydrate formation in the presence of water, wherein a mixture comprising the hydrocarbon and water is contacted with a composition of the previous paragraph.

DETAILED DESCRIPTIONS OF THE INVENTION

This invention relates a method and a composition used therein for inhibiting, retarding, mitigating, reducing, controlling and/or delaying formation of hydrocarbon hydrates or agglomerates of hydrates. The method may be applied to prevent or reduce or mitigate plugging of conduits, pipes, transfer lines, valves, and other places or equipment where hydrocarbon hydrate solids may form under the conditions.

The term "inhibiting" is used herein in a broad and general sense to mean any improvement in preventing, controlling, delaying, reducing or mitigating the formation, growth and/or agglomeration of hydrocarbon hydrates, particularly light hydrocarbon gas hydrates in any manner, including, but not limited to kinetically, thermodynamically, by dissolution, by breaking up, other mechanisms, or any combinations thereof.

The term "formation" or "forming" relating to hydrates is used herein in a broad and general manner to include, but are not limited to, any formation of hydrate solids from water and hydrocarbon(s) or hydrocarbon gas(es), growth of hydrocarbon hydrate solids, agglomeration of hydrocarbon hydrates, accumulation of hydrocarbon hydrates on surfaces, any deterioration of hydrate solids plugging or other problems in a system and combinations thereof.

The present method is useful for inhibiting hydrate formation for many hydrocarbons and hydrocarbon mixtures. The method is particularly useful for lighter or low-boiling, $C_1$–$C_5$, hydrocarbon gases or gas mixtures at ambient conditions. Examples of such gases include methane, ethane, ethylene, acetylene, propane, propylene, methylacetylene, n-butane, isobutane, 1-butene, trans-2-butene, cis-2-butene, isobutene, butene mixtures, isopentane, pentenes and mixtures thereof. Other examples include various natural gas mixtures that are present in many gas and/or oil formations and natural gas liquids (NGL). The hydrates of all of these low-boiling hydrocarbons are also referred to as gas hydrates. The hydrocarbons may also comprise other compounds including, but not limited to CO, $CO_2$, COS, hydrogen, hydrogen sulfide, other compounds commonly found in gas/oil formations or processing plants, either naturally occurring or used in recovering/processing hydrocarbons from the formation or both, and mixtures thereof.

The method of the present invention involves contacting a suitable composition with a mixture comprising the hydrocarbon and water. The composition comprises a first amount of a quaternary onium compound and a second amount of an amine salt. When effective first amount and effective second amount are used, hydrocarbon hydrate formation is inhibited under conditions such hydrate formation is not inhibited in the absence of such effective first and second amounts. After the contacting and after the conditions no longer favor formation of gas hydrates, the method may further comprise, optionally, removing the composition, individual or certain components of the composition or other compounds or mixtures in the composition or the mixture comprising water and the hydrocarbons.

The contacting may be achieved by a number ways, including mixing, blending with mechanical mixing equipment or devices, stationary mixing setup or equipment, magnetic mixing or other suitable methods, other equipment and means known to one skilled in the art and combinations thereof to provide adequate contact and/or dispersion of the composition in the mixture. The contacting can be made in-line or offline or both. The various components of the composition may be mixed prior to or during contact, or both. As discussed, if needed or desired, the composition or some of its components may be optionally removed or separated mechanically, chemically, or by other methods known to one skilled in the art, or by a combination of these methods after the hydrate formation conditions are no longer present.

Because the present invention is particularly suitable for lower boiling hydrocarbons or hydrocarbon gases at ambient conditions with no more than five carbon atoms, the pressure of the condition is usually at or greater than atmospheric pressure. (i.e. $\geq$~101 kPa), preferably greater than about 1 MPa, and more preferably greater than about 5 MPa. The pressure in certain formation or processing plants or units could be much higher, say greater than about 20 MPa. There is no specific high pressure limit. The present method can be used at any pressure which allows formation of hydrocarbon gas hydrates.

The temperature of the condition for contacting is usually below, the same as, or not much higher than the ambient or room temperature. Lower temperatures tend to favor hydrate formation, thus requiring the treatment with the composition of the present invention. At much higher temperatures, however, hydrocarbon hydrates may not form, thus obviating the need of carrying out any treatments.

Suitable onium compounds for use in the composition for the present invention are defined to have a general structure of the following formula having a cation with a center atom X and an anion Y⁻:

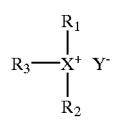

A wherein $R_1$ and $R_2$ each are independently selected from normal or branched alkyls containing a chain of at least 4 carbon atoms, with or without one or more substituents, or one or more heteroatoms;

$R_3$ is an organic moiety containing a chain of at least 4 carbon atoms, with or without one or more substituents, or one or more heteroatoms;

X is S, N—$R_4$ or P—$R_4$; and $R_4$, if present, is selected from H or an alkyl, aryl, alkylaryl, alkenylaryl or alkenyl group, preferably those having from about 1 to about 20 carbon atoms, with or without one or more substituents, or one or more heteroatoms.

Y⁻ may be selected from the group consisting of hydroxide ion (OH⁻), a halide ion such as Br⁻ and Cl⁻, a carboxylate ion such as benzoate ($C_6H_5COO^-$), sulfate ion ($SO_4^=$), organic sulfonate ion such as 4-toluene sulfonate and $CH_3SO_3^-$ and the like and mixtures thereof.

Ammonium and phosphonium compounds of the above formula may also be bound through $R_4$ to become pendant groups of a number of oxygen-containing polymers. Suitable oxygen-containing polymers include, but are not limited to polyacrylic acid, polymethacrylic acid, copolymers of acrylic and methacrylic acids, and polymers or co-polymers of poly-N-vinyl-2-pyrrolidone.

Alkyl ammonium and alkyl phosphonium compounds are preferred onium compounds for the composition of the present invention when $R_4$ is H or any alkyl or alkenyl group. In these preferred onium compounds, $R_3$ can be optionally selected from the group consisting of —($CH_2CHR_5$—O—)$_n$H and —($CH_2CH_2NH$—)$_m$H, wherein $R_5$ is H or methyl; n is an integer from about 5 to about 50; and m is an integer from 1 to about 5.

Examples of preferred cation moiety for the onium compounds include, but are not limited to, tetrapentylammonium, tripentylbutylammonium, triisopentylbutylammonium, tripentyldecylammonium, triisopentylammonium, tributyloctadecylammonium, tetrabutylphosphonium, tributyl(9-octadecenyl) phosphonium ions and mixtures thereof.

In accordance with formula A, examples of onium compounds include, but are not limited to, tributyldecylammonium, tributylundecylammonium, tributyldodecylammonium, tributyltridecylammonium, tributyltetradecylammonium, tributylpentadecylammonium, tributylhexadecylammonium, tributylhetpadecylammonium, tributyloctadecydecylammonium, tributylnonadecylammonium, tripentyldecylammonium, tripentylundecylammonium, tripentyldodecylammonium, tripentyltridecylammonium, tripentytetradecylammonium, tripentylpentadecylammonium, tripentylhexadecylammonium, tripentylheptadecylammonium, tripentyloctadecylammonium, tripentylnonadecylammonium, propyldibutyldecylammonium, propyldibutylundecylammonium, propyldibutyldodecylammonium, propyldibutyltridecylammonium, propyldibutyltetradecylammonium, propyldibutylpentadecylammonium, propyldibutylhexadecylammonium, propyldibutylheptadecylammonium, propyldibutyloctadecylammonium, propyldibutylnonadecylammonium, allyldibutyldecylammonium, allyldibutylundecylammonium, allyldibutyldodecylammonium, allyldibutyltridecylammonium, allyldibutyltetradecylammonium, allyldibutylpentadecylammonium, allyldibutyhexadecylammonium, allyldibutylheptadecylammonium, allyldibutyloctadecylammonium, allyldibutylnonadecylammonium, methallyldibutyldecylammonium, methallyldibutylundecylammonium, methallyldibutyldodecylammonium, methallyldibutyltridecylammonium, methallyldibutyltetradecylammonium, methallyldibutylpentadecylammonium, methallyldibutylhexadecylammonium, methallyldibutylheptadecylammonium, methallyldibutyloctadecylammonium, methallyldibutylnonadecylammonium, dibutyldidecylammonium, dibutyldiundecylammonium, dibutyldidodecylammonium, dibutylditridecylammonium, dibutylditetradecylammonium, dibutyldipentadecylammonium, dibutyldihexadecylammonium, dibutyldiheptadecylammonium, dibutyldioctadecylammonium and dibutyldinonadecylammonium salts, and mixtures thereof.

Additional preferred "onium" compounds include the phosphonium compounds corresponding to above ammonium compounds. These "onium" compounds include, but are not limited to tributyldecylphosphonium, tributylundecylphosphonium, tributyldodecylphosphonium, tributyltridecylphosphonium, tributyltetradecylphosphonium, tributylpentadecylphosphonium, tributylhexadecylphosphonium, tributylhetpadecylphosphonium, tributyloctadecydecylphosphonium, tributylnonadecylphosphonium, tripentyldecylphosphonium, tripentylundecylphosphonium, tripentyldodecylphosphonium, tripentyltridecylphosphonium, tripentytetradecylphosphonium, tripentylpentadecylphosphonium, tripentylhexadecylphosphonium, tripentylheptadecylphosphonium, tripentyloctadecylphosphonium, tripentylnonadecylphosphonium, propyldibutyldecylphosphonium, propyldibutylundecylphosphonium, propyldibutyldodecylphosphonium, propyldibutyltridecylphosphonium, propyldibutyltetradecylphosphonium, propyldibutylpentadecylphosphonium, propyldibutylhexadecylphosphonium, propyldibutylheptadecylphosphonium, propyldibutyloctadecylphosphonium, propyldibutylnonadecylphosphonium, allyldibutyldecylphosphonium, allyldibutylundecylphosphonium, allyldibutyldodecylphosphonium, allyldibutyltridecylphosphonium, allyldibutyltetradecylphosphonium, allyldibutylpentadecylphosphonium, allyldibutyhexadecylphosphonium, allyldibutylheptadecylphosphonium, allyldibutyloctadecylphosphonium, allyldibutylnonadecylphosphonium, methallyldibutyldecylphosphonium, methallyldibutylundecylphosphonium, methallyldibutyldodecylphosphonium, methallyldibutyltridecylphosphonium, methallyldibutyltetradecylphosphonium, methallyldibutylpentadecylphosphonium, methallyldibutylhexadecylphosphonium, methallyldibutylheptadecylphosphonium, methallyldibutyloctadecylphosphonium, methallyldibutylnonadecylphosphonium, dibutyldidecylphosphonium, dibutyldiundecylphosphonium, dibutyldidodecylphosphonium, dibutylditridecylphosphonium, dibutylditetradecylphosphonium, dibutyldipentadecylphosphonium, dibutyldihexadecylphosphonium, dibutyldiheptadecylphosphonium, dibutyldioctadecylphosphonium and dibutyldinonadecylphosphonium salts and mixtures thereof.

Also preferred for the present invention are onium compounds wherein zero to five of the $CH_2$ groups in the longest chains of the onium compound are replaced with one or more of the following groups $CHCH_3$, CHOH, O, C=O. Thus the onium compound may contain methyl groups, hydroxyl groups, ether groups or linkages, ester groups or linkages, and/or ketone groups. One advantage of such materials is that oxygen atoms in the chains, when present, can improve the biodegradability of the onium compounds. Also, two adjacent $CH_2$ groups in the longest chains of the onium compound may be replaced with a CH=CH group such that the onium compound may contain one or more carbon to carbon double bonds. The "onium" compounds are named after the parent hydrocarbon and the replacement group(s) in the longest chain are then stated. Thus

CH₃CH₂CH₂CH₂CH₂CH₂CH₂O CH₂CH₂CH₂CH₂N(CH₂CH₂CH₂CH₃)₃ is referred to as tributyldodecylammonium where C5 is replaced with O. Examples of onium compounds where CH₂ groups in the longest chains are replaced with CHCH₃, CHOH, O, C=O, or CH=CH groups include but are not limited to tributyldecylammonium, tributylundecylammonium, tributyldodecylammonium, tributyltridecylammonium, tributyltetradecylammonium, tributylpentadecylammonium, tributylhexadecylammonium, tributylhetpadecylammonium, tributyloctadecydecylammonium, tributylnonadecylammonium, tripentyldecylammonium, tripentylundecylammonium, tripentyldodecylammonium, tripentyltridecylammonium, tripentylpentadecylammonium, tripentylhexadecylammonium, tripentylheptadecylammonium, tripentyloctadecylammonium, tripentylnonadecylammonium, propyldibutyldecylammonium, propyldibutylundecylammonium, propyldibutyldodecylammonium, propyldibutyltridecylammonium, propyldibutyltetradecylammonium, propyldibutylpentadecylammonium, propyldibutylhexadecylammonium, propyldibutylheptadecylammonium, propyldibutyloctadecylammonium, propyldibutylnonadecylammonium, allyldibutyldecylammonium, allyldibutylundecylammonium, allyldibutyldodecylammonium, allyldibutyltridecylammonium, allyldibutyltetradecylammonium, allyldibutylpentadecylammonium, allyldibutyhexadecylammonium, allyldibutylheptadecylammonium, allyldibutyloctadecylammonium, allyldibutylnonadecylammonium, methallyldibutyldecylammonium, methallyldibutylundecylammonium, methallyldibutyldodecylammonium, methallyldibutyltridecylammonium, methallyldibutyltetradecylammonium, methallyldibutylpentadecylammonium, methallyldibutylhexadecylammonium, methallyldibutylheptadecylammonium, methallyldibutyloctadecylammonium, methallyldibutylnonadecylammonium, dibutyldidecylammonium, dibutyldiundecylammonium, dibutyldidodecylammonium, dibutylditridecylammonium, dibutylditetradecylammonium, dibutyldipentadecylammonium, dibutyldihexadecylammonium, dibutyldiheptadecylammonium, dibutyldioctadecylammonium and dibutyldinonadecylammonium salts where C2 is replaced with CHOH and C4 is replaced with O;

tributyldecylammonium, tributylundecylammonium, tributyldodecylammonium, tributyltridecylammonium, tributyltetradecylammonium, tributylpentadecylammonium, tributylhexadecylammonium, tributylhetpadecylammonium, tributyloctadecydecylammonium, tributylnonadecylammonium, tripentyldecylammonium, tripentylundecylammonium, tripentyldodecylammonium, tripentyltridecylammonium, tripentytetradecylammonium, tripentylpentadecylammonium, tripentylhexadecylammonium, tripentylheptadecylammonium, tripentyloctadecylammonium, tripentylnonadecylammonium, propyldibutyldecylammonium, propyldibutyldecylammonium, propyldibutyldodecylammonium, propyldibutyltridecylammonium, propyldibutyltetradecylammonium, propyldibutylpentadecylammonium, propyldibutylhexadecylammonium, propyldibutylheptadecylammonium, propyldibutyloctadecylammonium, propyldibutylnonadecylammonium, allyldibutyldecylammonium, allyldibutylundecylammonium, allyldibutyldodecylammonium, allyldibutyltridecylammonium, allyldibutyltetradecylammonium, allyldibutylpentadecylammonium, allyldibutyhexadecylammonium, allyldibutylheptadecylammonium, allyldibutyloctadecylammonium, allyldibutylnonadecylammonium, methallyldibutyldecylammonium, methallyldibutylundecylammonium, methallyldibutyldodecylammonium, methallyldibutyltridecylammonium, methallyldibutyltetradecylammonium, methallyldibutylpentadecylammonium, methallyldibutylhexadecylammonium, methallyldibutylheptadecylammonium, methallyldibutyloctadecylammonium, methallyldibutylnonadecylammonium, dibutyldidecylammonium, dibutyldiundecylammonium, dibutyldidodecylammonium, dibutylditridecylammonium, dibutylditetradecylammonium, dibutyldipentadecylammonium, dibutyldihexadecylammonium, dibutyldiheptadecylammonium, dibutyldioctadecylammonium and dibutyldinonadecylammonium salts where C2 is replaced with CHCH₃, C3 is replaced with O and C4 is replaced with C=O;

tributyldecylammonium, tributylundecylammonium, tributyldodecylammonium, tributyltridecylammonium, tributyltetradecylammonium, tributylpentadecylammonium, tributylhexadecylammonium, tributylhetpadecylammonium, tributyloctadecydecylammonium, tributylnonadecylammonium, tripentyldecylammonium, tripentylundecylammonium, tripentyldodecylammonium, tripentyltridecylammonium, tripentytetradecylammonium, tripentylpentadecylammonium, tripentylhexadecylammonium, tripentylheptadecylammonium, tripentyloctadecylammonium, tripentylnonadecylammonium, propyldibutyldecylammonium,
propyldibutylundecylammonium,
propyldibutyldodecylammonium,
propyldibutyltridecylammonium,
propyldibutyltetradecylammonium,
propyldibutylpentadecylammonium,
propyldibutylhexadecylammonium,
propyldibutylheptadecylammonium,
propyldibutyloctadecylammonium,
propyldibutylnonadecylammonium,
allyldibutyldecylammonium,
allyldibutylundecylammonium,
allyldibutyldodecylammonium,
allyldibutyltridecylammonium,
allyldibutyltetradecylammonium,
allyldibutylpentadecylammonium,
allyldibutyhexadecylammonium,
allyldibutylheptadecylammonium,
allyldibutyloctadecylammonium,
allyldibutylnonadecylammonium,
methallyldibutyldecylammonium,
methallyldibutylundecylammonium,
methallyldibutyldodecylammonium,
methallyldibutyltridecylammonium,
methallyldibutyltetradecylammonium,
methallyldibutylpentadecylammonium,
methallyldibutylhexadecylammonium,
methallyldibutylheptadecylammonium,
methallyldibutyloctadecylammonium,
methallyldibutylnonadecylammonium,
dibutyldidecylammonium,
dibutyldiundecylammonium,
dibutyldidodecylammonium,
dibutylditridecylammonium,
dibutylditetradecylammonium,
dibutyldipentadecylammonium,
dibutyldihexadecylammonium,
dibutyldiheptadecylammonium, dibutyldioctadecylammonium and dibutyldinonadecylammonium salts where C3 is replaced with O and C4 is replaced with C=O;

tributyldecylammonium, tributylundecylammonium, tributyldodecylammonium, tributyltridecylammonium, tributyltetradecylammonium, tributylpentadecylammonium, tributylhexadecylammonium, tributylhetpadecylammonium, tributyloctadecydecylammonium, tributylnonadecylammonium, tripentyldecylammonium, tripentylundecylammonium, tripentyldodecylammonium, tripentyltridecylammonium, tripentytetradecylammonium, tripentylpentadecylammonium, tripentylhexadecylammonium, tripentylheptadecylammonium, tripentyloctadecylammonium, tripentylnonadecylammonium, propyldibutyltridecylammonium, propyldibutyldecylammonium, propyldibutyldodecylammonium, propyldibutyltridecylammonium, propyldibutyltetradecylammonium, propyldibutylpentadecylammonium, propyldibutylhexadecylammonium, propyldibutylheptadecylammonium, propyldibutyloctadecylammonium,
propyldibutylnonadecylammonium,
allyldibutyldecylammonium,
allyldibutylundecylammonium,
allyldibutyldodecylammonium,
allyldibutyltridecylammonium,
allyldibutyltetradecylammonium,
allyldibutylpentadecylammonium,
allyldibutyhexadecylammonium,
allyldibutylheptadecylammonium,
allyldibutyloctadecylammonium,
allyldibutylnonadecylammonium,
methallyldibutyldecylammonium,
methallyldibutylundecylammonium,
methallyldibutyldodecylammonium,
methallyldibutyltridecylammonium,
methallyldibutyltetradecylammonium,
methallyldibutylpentadecylammonium,
methallyldibutylhexadecylammonium,
methallyldibutylheptadecylammonium,
methallyldibutyloctadecylammonium,
methallyldibutylnonadecylammonium,
dibutyldidecylammonium,
dibutyldiundecylammonium, dibutyldidodecylammonium, dibutylditridecylammonium,
dibutylditetradecylammonium,
dibutyldipentadecylammonium,
dibutyldihexadecylammonium,
dibutyldiheptadecylammonium, dibutyldioctadecylammonium and dibutyldinonadecylammonium salts where C3 is replaced with O;

tributyldecylammonium, tributylundecylammonium, tributyldodecylammonium, tributyltridecylammonium, tributyltetradecylammonium, tributylpentadecylammonium, tributylhexadecylammonium, tributylhetpadecylammonium, tributyloctadecydecylammonium, tributylnonadecylammonium, tripentyldecylammonium, tripentylundecylammonium, tripentyldodecylammonium, tripentyltridecylammonium, tripentytetradecylammonium, tripentylpentadecylammonium, tripentylhexadecylammonium, tripentylheptadecylammonium, tripentyloctadecylammonium, tripentylnonadecylammonium, propyldibutyltridecylammonium, propyldibutylundecylammonium, propyldibutyldodecylammonium, propyldibutyltridecylammonium, propyldibutyltetradecylammonium, propyldibutylpentadecylammonium, propyldibutylhexadecylammonium, propyldibutylheptadecylammonium, propyldibutyloctadecylammonium, propyldibutylnonadecylammonium, allyldibutyldecylammonium, allyldibutylundecylammonium, allyldibutyldodecylammonium, allyldibutyltridecylammonium, allyldibutyltetradecylammonium, allyldibutylpentadecylammonium, allyldibutyhexadecylammonium, allyldibutylheptadecylammonium, allyldibutyloctadecylammonium, allyldibutylnonadecylammonium, methallyldibutyldecylammonium,
methallyldibutylundecylammonium,
methallyldibutyldodecylammonium,
methallyldibutyltridecylammonium,
methallyldibutyltetradecylammonium,
methallyldibutylpentadecylammonium,
methallyldibutylhexadecylammonium,
methallyldibutylheptadecylammonium,
methallyldibutyloctadecylammonium,
methallyldibutylnonadecylammonium,
dibutyldidecylammonium,
dibutyldiundecylammonium,
dibutyldidodecylammonium,
dibutylditridecylammonium,
dibutylditetradecylammonium,
dibutyldipentadecylammonium,
dibutyldihexadecylammonium,
dibutyldiheptadecylammonium, dibutyldioctadecylammonium and dibutyldinonadecylammonium salts where C3 is replaced with O and C5 is replaced with CHOH; and
tributyldodecylammonium, tributylundecylammonium, tributyldodecylammonium, tributyltridecylammonium,
tributyltetradecylammonium,
tributylpentadecylammonium,
tributylhexadecylammonium,
tributylhetpadecylammonium,
tributyloctadecydecylammonium,
tributylnonadecylammonium,
tripentyldecylammonium, tripentylundecylammonium,
tripentyldodecylammonium,
tripentyltridecylammonium,
tripentytetradecylammonium,
tripentylpentadecylammonium,
tripentylhexadecylammonium,
tripentylheptadecylammonium,
tripentyloctadecylammonium,
tripentylnonadecylammonium,
propyldibutyldecylammonium,
propyldibutylundecylammonium,
propyldibutyldodecylammonium,
propyldibutyltridecylammonium,
propyldibutyltetradecylammonium,
propyldibutylpentadecylammonium,
propyldibutylhexadecylammonium,
propyldibutylheptadecylammonium,
propyldibutyloctadecylammonium,
propyldibutylnonadecylammonium,
allyldibutyldecylammonium,
allyldibutylundecylammonium,
allyldibutyldodecylammonium,
allyldibutyltridecylammonium,
allyldibutyltetradecylammonium,
allyldibutylpentadecylammonium,
allyldibutyhexadecylammonium,
allyldibutylheptadecylammonium,
allyldibutyloctadecylammonium,
allyldibutylnonadecylammonium,
methallyldibutyldecylammonium,
methallyldibutylundecylammonium,
methallyldibutyldodecylammonium,
methallyldibutyltridecylammonium,
methallyldibutyltetradecylammonium,
methallyldibutylpentadecylammonium,
methallyldibutylhexadecylammonium,
methallyldibutylheptadecylammonium,
methallyldibutyloctadecylammonium,
methallyldibutylnonadecylammonium,
dibutyldidecylammonium,
dibutyldiundecylammonium,
dibutyldidodecylammonium,
dibutylditridecylammonium,
dibutylditetradecylammonium,
dibutyldipentadecylammonium,
dibutyldihexadecylammonium,
dibutyldiheptadecylammonium, dibutyldioctadecylammonium and dibutyldinonadecylammonium salts where C9 and C10 are replaced with CH=CH.

Also suitable are phosphonium compounds corresponding to these ammonium compounds. Finally, mixtures of such onium compounds are suitable or in many cases preferred for use with the present invention. A number of other examples have been disclosed and described in U.S. Pat. Nos. 5,460,728 and 5,648,575 and such compounds can also be used with the present invention.

The composition of the present invention also comprises an amine salt. The term "amine salt" is used to mean herein that it is an ionic product with a nitrogen-containing cationic moiety and acid-derived anionic moiety. Accordingly, in most, if not all cases, the amine salt component of the composition may be readily or conveniently prepared by combining or reacting at least one amine, i.e. a nitrogen-containing base, with and at least one acid. Sometimes, however, it may be possible or even preferred to use starting materials different from the nitrogen-containing amine base and the acid themselves.

Suitable nitrogen-containing bases, generally referred to just as "amines," include those with a total of twelve or fewer, preferably nine or fewer, carbon atoms in a particular molecule. The general formulas "B" and "C" represent examples of preferred amines:

$R^aR^bR^cN$                 B

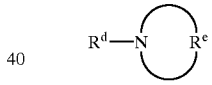

C wherein $R^a$, $R^b$, $R^c$, and $R^d$ are independently selected from the group consisting of H, $C_1$–$C_3$ alkyls and OH substituted $C_1$–$C_3$ alkyls. $R^e$ is selected from the group consisting of —$(CH_2)_m$— and —$(CH_2)_n$—Z—$(CH_2)_p$—, wherein Z is selected from O, S and CHR$^f$ and m is selected from 3 to 7; n, from 1 to 3; and p, from 1 to 4. $R^f$ is selected from H, $C_1$–$C_3$ alkyls and OH substituted $C_1$–$C_3$ alkyls.

More specific examples of preferred amines include, but are not limited to NH$_3$, methylamine, ethylamine, n-propylamine, iso-propylamine, dimethylamine, diethylamine, di-n-propylamine, trimethylamine, triethylamine, tri-n-propylamine, ethanolamine, diethanolamine, triethanolamine, methyl ethanolamine, ethyl ethanolamine, propyl ethanolamine, methyl diethanolamine, ethyl diethanolamine, dimethyl ethanolamine, diethyl ethanolamine, morpholine, N-methylmorpholine, N-ethylmorpholine, N-propylmorpholine and mixtures thereof.

Suitable acids for the corresponding anionic moiety of the amine salt include, but are not limited to, lower carboxylic acids having four or fewer carbon atoms and inorganic acids. Examples of preferred lower carboxylic acids include formic acid, acetic acid, propionic acid, butyric acid, glycolic acid, malonic acid, succinic acid, acrylic acid, substituted carboxylic acids such as trifluoroacetic acid, methanesulfonic acid and mixtures thereof. Examples of preferred inorganic acids include nitric acid, HCl, HBr and chemically compatible mixtures thereof.

The amine salts may be prepared by a number of methods under various conditions known to those skilled in the art. For example, the amine salts may be prepared by directly combining a selected amine or amine mixture with a selected acid or acid mixture. Alternatively, other starting materials, derivatives of the amine and/or the acid may be used to replace the amine and or the acid. For example, esters, anhydrides or acyl halides may be used in place of the acids for making the amine salts. Preferably, many of these reactions are carried out in a nonaqueous system.

The amount of the onium compound, also referred to as "first amount" in the composition should be effective, in combination with an effective amount, also referred to as "second amount," of the amine salt, under the conditions to effect inhibition of formation, agglomeration, growth or other unfavorable changes (collectively referred to as formation) of hydrates or to dissolve, breakup or otherwise convert hydrates existing in the system.

Based on the total volume of the composition, the (first) amount of the onium compound should be in the range of from about 5 volume to about 75 volume %, preferably from about 10 volume % to about 65 volume %. Similarly, the (second) amount of the amine salt in the composition should be effective, in combination with an effective amount of the amine salt, under the conditions to effect the inhibition of the formation of hydrates. Based on the total volume of the composition, the (second) amount of the amine salt should be in the range of from about 10 volume to about 95 volume %, preferably from about 15 volume % to about 85 volume %.

In addition to the onium compound and the amine salt, the composition may further comprise other additional components, preferably liquids. Solvents are examples of such additional components. Suitable solvents include, but are not limited to water; at least one oxygenated compound selected from $C_1$–$C_6$ alcohols, $C_2$–$C_6$ glycols, $C_1$–$C_6$ mono-aliphatic, preferably mono-alkyl, ethers of $C_2$–$C_6$ glycol, glycerin, $C_1$–$C_6$ mono-aliphatic, particularly mono-alkyl, ethers of glycerin, $C_1$–$C_6$ di-aliphatic, particularly dialkyl, ethers of glycerin, glycerin esters of $C_1$–$C_6$ carboxylate; tetrahydrofuran; N-methylpyrrolidone; sulfolane; $C_3$–$C_{10}$ ketones, and mixtures thereof. Examples of preferred solvents include water and liquid oxygenated materials such as methanol, ethanol, propanol, glycols like ethylene glycol, 1,2-propylene glycol, 1,3-propylene glycol, glycerin, esters and ethers of glycerin, CELLOSOLVE® (2-ethoxyethanol), CELLOSOLVE derivatives, 2-methoxyethanol, ethoxylated propylene glycols, ketones such as cyclohexanone and diisobutylketone, and mixtures thereof. The solvent is present in the composition in the range of from 0% to about 85%, preferably from about 0% to about 65%, of the total composition, based on volume. CELLOSOLVE is a registered trademark of Union Carbide Corporation.

Because many of the onium compounds and the amine salts disclosed herein are solids under ambient conditions, it is often preferred to use a suitable solvent as described above in the composition. This allows the formation of a homogeneous or uniform solution, suspension, emulsion or a combination of these, of all the components for easier mixing or distributing or dispersing the composition in the hydrocarbon/water fluid or system to be treated. As a result, more efficient and/or favorable contacting of the composition with the mixture comprising water and the hydrocarbon can be effected.

The present invention also may be used in combination with other methods or processes, which have been known to one skilled in the art as discussed in the background to help inhibit formation of hydrates.

The following example only illustrates certain specific embodiments of the invention. It is not meant to limit the spirit or scope of the present invention in any manner. When the example and the associated results in the Table are read together with the rest of the written description of specification and the claims, one skilled in the art would more appreciate and better understood the instant invention and its other embodiments.

EXAMPLE

Hydrocarbon gas hydrates typically require high pressures to form. The laboratory procedures are designed to accommodate this requirement by using a high pressure and a suitable temperature. The difference between the maximum temperature at which the hydrates can form and a lower temperature at which the experiments were carried out is termed "subcooling." In order for the hydrates to form within a reasonably short length of time, some subcooling and/or agitation is generally needed. Hydrocarbon hydrates become a serious problem when they form an immobile mass of solids and crystals plugging the conduits, pipelines, valves and other equipment. Accordingly, a visual observation method is used to judge the results of the experiments. These observations are then translated into a ranking system, which is detailed below in the Table.

The experiments are carried out using 4.00 ml de-ionized (DI) water, 8.00 ml of n-heptane, and 5% propane in methane at 1400 psig (9.75 MPa) to prepare and admixture at equilibrium pressure at ambient room temperature (about 25° C.), followed by placing the admixture in a cooled bath set at 40° F. (about 4.5° C.).

The general procedure of the experiments conducted is as follows. The selected amounts of water, hydrate inhibitor and liquid hydrocarbon phase are introduced into a cylindrical high pressure stainless cell with glass windows. The cell also contains a stainless steel ball to provide agitation. The total volume of the cell is about 35 ml, including all the ancillary plumbing on the cylinder side of the shutoff valve.

A selected mixed hydrocarbon gas at a fixed pressure is introduced into the cell and cell is shaken to allow the gas to dissolve in the liquids and come to equilibrium. This dissolution results in a pressure decrease and an increase in the volume of the hydrocarbon liquids. More gas is introduced and the process is repeated until a desired equilibrium gas pressure is reached under the reaction conditions. Ambient temperature is usually used for this part of the procedure. Many cells can be set up before the tests begin.

The cells prepared are then placed in a large, temperature-controlled and cooled water bath. After about 23±1 hours, the cells are examined and the conditions are judged according to the footnotes below the Table. The cells are than rocked for five minutes to provide agitation and they are examined and judged again. The cells are then rocked for another 25 minutes (for a total of 30 minutes) and they are examined and judged again.

The results from these experiments are shown below in the Table with the ranking criteria set forth below the Table. RE 4136, a quaternary ammonium compound, is available commercially from Baker Petrolite.

TABLE*

| Run No. | RE4136 | Methanol (ml) | Ethanolamine Acetate (ml) | Ethanolamine Propionate (ml) | Total Additive/water (volume %) | 23 hour shut in | 5-minute rock | 30-minute rock | Worst Condition Result* |
|---|---|---|---|---|---|---|---|---|---|
| a | | | 0.300 | | 7.50 | A | F | F | F |
| b | | 0.120 | 0.180 | | 7.50 | F | F | F | F |
| c | | 0.300 | | | 7.50 | A | F | F | F |
| d | 0.015 | | 0.285 | | 7.50 | F | F | F | F |
| e | 0.015 | 0.105 | 0.150 | | 6.75 | A | B | F | F |
| f | 0.030 | 0.030 | 0.240 | | 7.50 | A | A | C | C |
| g | 0.030 | 0.090 | 0.180 | | 7.50 | A | A | D | D |
| h | 0.030 | 0.120 | 0.150 | | 7.50 | A | A- | D+ | D+ |
| i | 0.030 | 0.150 | 0.120 | | 7.50 | A | A | D- | D- |
| j | 0.030 | 0.150 | 0.120 | | 7.50 | C | C- | B | C- |
| k | 0.030 | 0.210 | 0.060 | | 7.50 | A | A- | B | B |
| l | 0.045 | | 0.255 | | 7.50 | A | A | D+ | D+ |
| m | 0.045 | 0.075 | 0.180 | | 7.50 | A | B | C | C |
| n | 0.048 | 0.102 | 0.150 | | 7.50 | A | C- | D | D |
| o | 0.060 | | | | 1.50 | A | F | F | F |
| p | 0.060 | 0.120 | 0.120 | | 7.50 | A | B | C | C |
| q | 0.060 | 0.160 | 0.080 | | 7.50 | B+ | A- | B | B |
| r | 0.060 | 0.180 | 0.060 | | 7.50 | B+ | C- | D | D |
| s | 0.060 | 0.210 | 0.030 | | 7.50 | B | C- | B | C- |
| t | 0.080 | 0.131 | | 0.089 | 7.50 | B | C- | C | C- |
| u | 0.080 | 0.140 | 0.080 | | 7.50 | B | C | C- | C- |
| v | 0.090 | 0.180 | 0.030 | | 7.50 | A | C | D- | D- |
| w | 0.120 | | | | 3.00 | D- | F+ | C | F+ |
| x | 0.300 | | | | 7.50 | B | C | B | C |

*The results are tabulated on a scale from A to F (no E rankings), with A being the best and F being the worst. The symbols + and − are appended to indicate tests that are better or worse respectively than the mid point of the ranking, but they did not belong to the next category. Rankings A+ and F− were not used. Descriptions of the ranking criteria are:
A No visible crystals. No solid deposits on glass or steel. Two distinct liquid phases.
B No sold deposits on glass or steel. Two low viscosity liquid phases. Few crystals not larger than 1 mm, or hazy systems where hydrate crystals are forming but are too small to distinguish with the unaided eye. No evidence of plugs in the system.
C No solid deposits on glass or steel. Often some increases in liquid viscosities, but still free flowing. Small crystals not agglomerating to form a plug, or a milky or emulsified single phase system. Some slight slush or silt may form, but it must be very mobile. No evidence of plugs in the system.
D No solid deposits on glass or steel. A heavy slush or silt is present, or there is a distinct increase in liquid viscosities. A long pipeline system would flow with difficulty. No evidence of immobile plugs in the system.
Large immobile agglomerations of crystals that interfere with the flow of liquids are present. The ball inside the cell to provide agitation during rocking is usually immobile. Deposits stuck on glass or steel.
The worst observed result of the three tests (23 hour, 5-min and 30-min).

The example and the result are intended for illustration purposes only. They are not intended and should not br interpreted to limit either the spirit or the scope of the present invention, which are defined by the entire written description and claims.

What is claimed:

1. A method for inhibiting formation of hydrocarbon hydrates, the method comprising:

providing a mixture comprising water and a hydrocarbon; and contacting a composition comprising a first amount of an onium compound and a second amount of an amine salt with the mixture under conditions effective to form the hydrocarbon hydrates in the absence of the composition, wherein:

the first amount of the onium compound and the second amount of the amine salt in the composition are effective in inhibiting the formation of the hydrocarbon hydrates under the conditions;

the hydrocarbon has one to five carbon atoms; and the cation moiety of the amine salt is derived from an amine selected from group consisting of amines having the general formula:

$$R^a R^b R^c N, \quad (a)$$

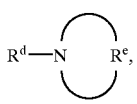

and mixtures thereof, and wherein $R^a$, $R^b$, $R^c$, and $R^d$ are independently selected from the group consisting of H, $C_1$–$C_3$ alkyls and OH substituted $C_1$–$C_3$ alkyls; and $R^e$ is selected from the group consisting of —$(CH_2)_m$— and —$(CH_2)_n$—Z—$(CH_2)_p$—, wherein Z is selected from O, S and $CHR^f$; m is from 3 to 7; n is from 1 to 3; p is from 1 to 4; and $R^f$ is selected from H, $C_1$–$C_3$ alkyls and OH substituted $C_1$–$C_3$ alkyls.

2. The method of claim 1, wherein the amine salt comprises a cation moiety selected from the group consisting of ammonium ion, organoammonium ion, and mixtures thereof.

3. The method of claim 1, wherein the hydrocarbon is selected from the group consisting of methane, ethane, propane, n-butane, isobutane, natural gas and mixtures thereof.

4. The method of claim 1, wherein the amine is selected from the group consisting of $NH_3$, methylamine, ethylamine, n-propylamine, iso-propylamine, dimethylamine, diethylamine, di-n-propylamine, trimethylamine, triethylamine, tri-n-propylamine, ethanolamine, diethanolamine, triethanolamine, methyl ethanolamine, ethyl ethanolamine, methyl diethanolamine, ethyl diethanolamine, dimethyl ethanolamine, diethyl ethanolamine, morpholine, N-methylmorpholine, N-ethylmorpholine and mixtures thereof.

5. The method of claim 1, wherein the composition further comprises a solvent selected from the group consisting of water; at least one oxygenate selected from $C_1$–$C_6$ alcohols, $C_2$–$C_6$ glycols, $C_1$–$C_6$ mono-alkyl ethers of $C_2$–$C_6$ glycol, glycerin, $C_1$–$C_6$ mono-alkyl ethers of glycerin, $C_1$–$C_6$ dialkyl ethers of glycerin, glycerin esters of $C_1$–$C_6$ carboxylate, $C_3$–$C_{10}$ ketones; and mixtures thereof.

6. The method of claim 1, wherein the onium compound has a structure of the following formula having a cation and an anion $Y^-$:

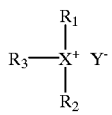

wherein $R_1$ and $R_2$ each are independently selected from normal or branched alkyls containing a chain of at least 4 carbon atoms, with or without one or more substituents, or one or more heteroatoms;

$R_3$ is an organic moiety containing a chain of at least 4 carbon atoms, with or without one or more substituents, or one or more heteroatoms;

X is S, N—$R_4$ or P—$R_4$;

$R_4$, if present, is selected from H or an alkyl, aryl, alkylaryl, alkenylaryl or alkenyl group; and $Y^-$ is selected from the group consisting of hydroxide ion ($OH^-$), halide ions, carboxylate ions, sulfate ion, organic sulfonate ions, and mixtures thereof.

7. The method of claim 6, wherein the onium ion is selected from the group consisting of tetrabutylammonium chloride, tetrabutylammonium bromide, tributylisopentylammonium bromide, tributylpentylammonium bromide, tributyltetradecylammonium bromide, tetrapentylammonium bromide, tripentylbutylammonium bromide, triisopentylbutylammonium bromide, tripentyldecylammonium bromide, triisopentylammonium bromide, tributyldecylammonium bromide, tributyldodecylammonium bromide, 1,6-di(tributylammonium)hexamethylene dibromide, 1,10-di(tripentylammonium)-decamethylene dibromide, tripentylammonium sulfate, dibutyldecylammonium sulfate, triisopentylammonium sulfate, tetrabutylammonium toluene-4-sulfonate, tetrabutylphosphonium chloride, tributylhexadecylphosphonium bromide, tributyl(9-octadecenyl)phosphonium bromide, butyltriphenylphosphonium bromide and mixtures thereof.

8. The method of claim 1 wherein the first amount of the onium compound is in the range of from about 5 volume % to about 75 volume %; and the second amount of the amine salt in the range of from about 10 volume % to about 95 volume %, based on total volume of the composition.

9. The method of claim 1 additionally comprising contacting the composition with a third amount of solvent wherein the first amount of the onium compound is in the range of from about 5 volume % to about 75 volume %; the second amount of the amine salt in the range of from about 10 volume % to about 95 volume %, and the third amount of solvent is the range of from 0 volume % to about 85 volume %, all based on total volume of the composition.

10. A composition for inhibiting formation of hydrocarbon hydrates from a mixture comprising water and a hydrocarbon, the composition comprising a first amount of an onium compound and a second amount of an amine salt, wherein the amine salt comprises a cation moiety and an anion moiety, the cation moiety is derived from an amine selected from group consisting of amines having the general formula:

$R^a R^b R^c N$,  (a)

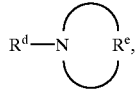 (b)

and mixtures thereof, wherein $R^a$, $R^b$, $R^c$, and $R^d$ are independently selected from the group consisting of H, $C_1$–$C_3$ alkyls and OH substituted $C_1$–$C_3$ alkyls; $R^e$ is selected from the group consisting of —$(CH_2)_m$— and —$(CH_2)_n$—Z—$(CH_2)_p$—, wherein Z is selected from O, S and $CHR^f$ and m is selected from 3 to 7; n, from 1 to 3; and p, from 1 to 4; $R^f$ is selected from H, $C_1$–$C_3$ alkyls and OH substituted $C_1$–$C_3$ alkyls.

11. The composition of claim 10, further comprising a third amount of a solvent.

12. The composition of claim 11, wherein the onium compound is selected from the group consisting of tetrabutylammonium chloride, tetrabutylammonium bromide, tributylisopentylammonium bromide, tributylpentylammonium bromide, tributyltetradecylammonium bromide, tetrapentylammonium bromide, tripentylbutylammonium bromide, triisopentylbutylammonium bromide, tripentyldecylammonium bromide, triisopentylammonium bromide, tributyldecylammonium bromide, triibutyldodecylammonium bromide, 1,6-di(tributylammonium)hexamethylene dibromide, 1,10-di(tripentylammonium)-decamethylene dibromide, tripentylammonium sulfate, dibutyldecylammonium sulfate, triisopentylammonium sulfate, tetrabutylammonium toluene-4-sulfonate, tetrabutylphosphonium chloride tributylhexadecylhexadecylphosphonium bromide, tributyl(9-octadecenyl)phosphonium bromide, butyltriphenylphosphonium bromide and mixtures thereof; and the cation moiety of the amine salt is derived from $NH_3$, methylene ethylamine, n-propylamine, isopropylamine, dimethylamine, diethylamine, di-n-propylamine, trimethylene, triethylamine, tri-n-propylamine, ethanolamine, diethanolamine, triethanolamine, methyl ethanolamine, ethyl ethanolamine, propyl, ethanolamine, methyl diethanolamine, ethyl diethanolamine, dimethyl ethanolamine, diethyl ethanolamine, morphine, N-methylorpholine, N-ethylmorpholine, N-propylmorpholine and mixtures thereof; and the anionic moiety is derived from formic acid, acetic acid, propionic acid, butyric acid, glycolic acid, nitric acid and mixtures thereof; and the solvent is selected from the group consisting of water, at least one oxygenate selected from $C_1$–$C_6$ alcohols, $C_2$–$C_6$ mono-alkyl ethers of $C_2$–$C_6$ glycol, glycerin, $C_1$–$C_6$ mono-alkyl ethers of glycerin, $C_1$–$C_6$ dialkyl ethers of gylcerin, glycerin esters of $C_1$–$C_6$ carboxylate; and mixtures thereof, wherein the first amount of the onium compound is in the range of from about 5 volume % to about 75 volume %; the second amount of the amine salt in the range of from about 10 volume % to about 85 volume %, all based on total volume of the composition.

13. The composition of claim 10, wherein the onium compound has a structure of the following formula having a cation and an anion Y⁻:

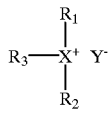

wherein $R_1$ and $R_2$ each are independently selected from normal or branched alkyls containing a chain of at least 4 carbon atoms, with or without one or more substituents, or one or more heteroatoms;

$R_3$ is an organic moiety containing a chain of at least 4 carbon atoms, with or without one or more substituents, or one or more heteroatoms;

X is S, N—$R_4$ or P—$R_4$;

$R_4$, if present, is selected from H or an alkyl, aryl, alkylaryl, alkenylaryl or alkenyl group; and Y⁻ is selected from the group consisting of hydroxide ion (OH⁻), halide ions, carboxylate ions, sulfate ion, organic sulfonate ions, and mixtures thereof.

14. The composition of claim 13, wherein the amine is selected from the group consisting of $NH_3$, methylamine, ethylamine, n-propylamine, iso-propylamine, dimethylamine, diethylamine, di-n-propylamine, trimethylamine, triethylamine, tri-n-propylamine, ethanolamine, diethanolamine, triethanolamine, methyl ethanolamine, ethyl ethanolamine, propyl ethanolamine, methyl diethanolamine, ethyl diethanolamine, dimethyl ethanolamine, diethyl ethanolamine, morpholine, N-methylmorpholine, N-ethylmorpholine, N-propylmorpholine and mixtures thereof; and the anionic moiety is derived from formic acid, acetic acid, propionic acid, butyric acid, glycolic acid, nitric acid and mixtures thereof.

15. A hydrocarbon composition inhibited against hydrocarbon hydrate formation in the presence of water, wherein a mixture comprising the hydrocarbon and water is contacted with a composition comprising a first amount of an onium compound and a second amount of an amine salt, wherein the amine salt comprises a cation moiety and an anion moiety, the cation moiety is derived from an amine of the following formula:

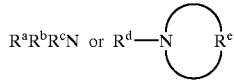

wherein $R^a$, $R^b$, $R^c$, and $R^d$ are independently selected from the group consisting of H, $C_1$–$C_3$ alkyls ad OH substituted $C_1$–$C_3$ alkyls; $R^e$ is selected from the group consisting of —$(CH_2)_m$— and —$(CH_2)_n$—Z—$(CH_2)_p$—, wherein Z is selected from O, S and $CHR^4$ and m is selected from 3 to 7; n, from 1 to 3; and p, from 1 to 4; $R^f$ is selected from H, $C_1$–$C_3$ alkyls and OH substituted $C_1$–$C_3$ alkyls; and

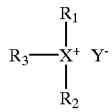

wherein $R_1$ and $R_2$ each are independently selected from normal or branched alkyls containing a first chain of at least 4 carbon atoms;

$R_3$ is an organic moiety containing a second chain of at least 4 carbon atoms;

X is selected from the group consisting of S, N—$R_4$ and P—$R_4$, wherein $R_4$ is selected from H and an alkyl, aryl, alkylaryl, alkenylaryl or alkenyl group having from about 8 to about 20 carbon atoms; and Y is selected from the group consisting of hydroxide ion, a halide ion, a carboxylate ion, sulfate ion, an orangic sulfonate ion and mixtures thereof.

* * * * *